(12) United States Patent
Fassina et al.

(10) Patent No.: US 6,344,362 B1
(45) Date of Patent: Feb. 5, 2002

(54) USE OF A RECOMBINANT PROTEIN AS RECEPTOR OF A HEPATITIS VIRUS

(75) Inventors: Giorgio Fassina, Milan; Sandro De Falco; Antonio Verdoliva, both of Naples; Menotti Ruvo, Trevico, all of (IT)

(73) Assignee: Ministero Dell Universita'E Della Ricerca Scientifica E Tecnologica (M.U.R.S.T.), Rome (IT)

( * ) Notice: Subject to any disclaimer, the term of this patent is extended or adjusted under 35 U.S.C. 154(b) by 0 days.

(21) Appl. No.: 09/266,910

(22) Filed: Mar. 12, 1999

Related U.S. Application Data
(60) Provisional application No. 60/110,014, filed on Nov. 25, 1998.

(30) Foreign Application Priority Data
Mar. 12, 1998 (IT) .......................................... MI98A0498

(51) Int. Cl.[7] ............................................. G01N 33/566
(52) U.S. Cl. .............................. 436/501; 435/5; 435/7.1; 435/69.1; 435/252.3; 530/350; 514/2; 514/44
(58) Field of Search .......................... 530/350; 435/7.1, 435/5, 69.1, 252.3; 514/2, 44; 436/501

(56) References Cited
FOREIGN PATENT DOCUMENTS
WO    WO 94/01554    1/1994

OTHER PUBLICATIONS
Bowie et al. Science 247(1306–1310) 1990.*
Wells Biochemistry 29(8509–8517) 1990.*
Ngo et al The Protein Folding Problem and Tertiary Structure, 1994.*
Tong, S. et al J. Virology 73:10(8696–8702) 1999.*
Kato, H. et al., GenBank Accession No. R25276, Jan. 8, 1993.*
Lewin, B. ed. Genes. p. 721, John Wiley and Sons, New York, 1983.*
Kato et al., GenBank # R25276, Jan. 1993.*
Anne DeJean et al, "Hepatitis B Virus DNA Integration in a Sequence Homologous to v–erb–A and Steroid Receptor Genes in a Hepatocellular Carcionma", Nature, vol. 322, pp. 70–72, (1986).
William P.J. Leenders et al, "Binding of the Major and Large HbsAg to Human Hepatocytes and Liver Plasma Membranes: Putative External and Internal Receptors for Infection and Secretion of Hepatitis B Virus", Hepatology, vol. 12, No. 1, pp. 141–147, (Jul. 1, 1990).
Yoshinori Suminami et al, "Squamous Cell Carcinoma Antigen is a New Member of the Serine Protease Inhibitors", Biochemical and Biophysical Research Communications, vol. 181, No. 1, pp. 51–58 (1991).
Daniel J. Kenan et al, "Exploring Molecular Diversity with Combinatorial Shape Libraries", TIBS Trends in Biochemical Sciences, vol. 19, No. 1, pp. 57–65, (Jan. 1, 1994).

* cited by examiner

Primary Examiner—Yvonne Eyler
Assistant Examiner—Michael Brannock
(74) Attorney, Agent, or Firm—Oblon, Spivak, McClelland, Maier & Neustadt, P.C.

(57) ABSTRACT

Disclosed herein are uses of a recombinant protein as a receptor for a hepatitis virus. Also disclosed are a nucleic acid coding for the receptor, a vector comprising a nucleic acid encoding the receptor, a host cell transformed or transfected with the nucleic acid, and a new recombinant protein having the biological property to act as a receptor for a hepatitis virus and a transgenic animal expressing the recombinant protein.

15 Claims, 2 Drawing Sheets

```
                                                        -7 GTTCACC
ATGAATTCACTCAGTGAAGCCAACACCAAGTTCATGTTCGACCTGTTCCAACAGTTCAGA  60
 M  N  S  L  S  E  A  N  T  K  F  M  F  D  L  F  Q  Q  F  R    20

AAATCAAAAGAGAACAACATCTTCTATTCCCCTATCAGCATCACATCAGCATTAGGGATG  120
 K  S  K  E  N  N  I  F  Y  S  P  I  S  I  T  S  A  L  G  M    40

GTCCTCTTAGGAGCCAAAGACAACACTGCACAACAGATTAAGAAGGTTCTTCACTTTGAT  180
 V  L  L  G  A  K  D  N  T  A  Q  Q  I  K  K  V  L  H  F  D    60

CAAGTCACAGAGAACACCACAGGAAAAGCTGCAACATATCATGTTGATAGGTCAGGAAAT  240
 Q  V  T  E  N  T  T  G  K  A  A  T  Y  H  V  D  R  S  G  N    80

GTTCATCACCAGTTTCAAAAGCTTCTGACTGAATTCAACAAATCCACTGATGCATATGAG  300
 V  H  H  Q  F  Q  K  L  L  T  E  F  N  K  S  T  D  A  Y  E   100

CTGAAGATCGCCAACAAGCTCTTCGGAGAAAAAACGTATCTATTTTTACAGGAATATTTA  360
 L  K  I  A  N  K  L  F  G  E  K  T  Y  L  F  L  Q  E  Y  L   120

GATGCCATCAAGAAATTTTACCAGACCAGTGTGGAATCTGTTGATTTTGCAAATGCTCCA  420
 D  A  I  K  K  F  Y  Q  T  S  V  E  S  V  D  F  A  N  A  P   140

GAAGAAAGTCGAAAGAAGATTAACTCCTGGGTGGAAAGTCAAACGAATGAAAAAATTAAA  480
 E  E  S  R  K  K  I  N  S  W  V  E  S  Q  T  N  E  K  I  K   160

AACCTAATTCCTGAAGGTAATATTGGCAGCAATACCACATTGGTTCTTGTGAACGCAATC  540
 N  L  I  P  E  G  N  I  G  S  N  T  T  L  V  L  V  N  A  I   180

TATTTCAAAGGGCAGTGGGAGAAGAAATTTAATAAAGAAGATACTAAAGAGGAAAAATTT  600
 Y  F  K  G  Q  W  E  K  K  F  N  K  E  D  T  K  E  E  K  F   200

TGGCCAAACAAGAATACATACAAGTCCATACAGATGATGAGGCAATACACATCTTTTCAT  660
 W  P  N  K  N  T  Y  K  S  I  Q  M  M  R  Q  Y  T  S  F  H   220

TTTGCCTCGCTGGAGGATGTACAGGCCAAGGTCCTGGAAATACCATACAAAGGCAAAGAT  720
 F  A  S  L  E  D  V  Q  A  K  V  L  E  I  P  Y  K  G  K  D   240

CTAAGCATGATTGTGTTGCTGCCAAATGAAATCGATGGTCTCCAGAAGCTTGAAGAGAAA  780
 L  S  M  I  V  L  L  P  N  E  I  D  G  L  Q  K  L  E  E  K   260

CTCACTGCTGAGAAATTGATGGAATGGACAAGTTTGCAGAATATGAGAGAGACACGTGTC  840
 L  T  A  E  K  L  M  E  W  T  S  L  Q  N  M  R  E  T  R  V   280

GATTTACACTTACCTCGGTTCAAAGTGGAAGAGAGCTATGACCTCAAGGACACGTTGAGA  900
 D  L  H  L  P  R  F  K  V  E  E  S  Y  D  L  K  D  T  L  R   300

ACCATGGGAATGGTGGATATCTTCAATGGGGATGCAGACCTCTCAGGCATGACCGGGAGC  960
 T  M  G  M  V  D  I  F  N  G  D  A  D  L  S  G  M  T  G  S   320

CGCGGTCTCGTGCTATCTGGAGTCCTACACAAGGCCTTTGTGGAGGTTACAGAGGAGGGA  1020
 R  G  L  V  L  S  G  V  L  H  K  A  F  V  E  V  T  E  E  G   340

GCAGAAGCTGCAGCTGCCACCGCTGTAGTAGGATTCGGATCATCACCTGCTTCAACTAAT  1080
 A  E  A  A  A  A  T  A  V  V  G  F  G  S  S  P  A  S  T  N   360

GAAGAGTTCCATTGTAATCACCCTTTCCTATTCTTCATAAGGCAAAATAAGACCAACAGC  1140
 E  E  F  H  C  N  H  P  F  L  F  F  I  R  Q  N  K  T  N  S   380

ATCCTCTTCTATGGCAGATTCTCATCCCCGTAGATGCAATTAGTCTGTCACTCCATTTGG  1200
 I  L  F  Y  G  R  F  S  S  P                                  390

AAAATGTTCACCTGCAGATGTTCTGGTAAACTGATTGC  1238
```

FIG. 1 (SEQ ID NOS: 1 and 3)

```
                                                        -7 GTTCACC
ATGAATTCACTCAGTGAAGCCAACACCAAGTTCATGTTCGACCTGTTCCAACAGTTCAGA 60
 M  N  S  L  S  E  A  N  T  K  F  M  F  D  L  F  Q  Q  F  R      20

AAATCAAAAGAGAACAACATCTTCTATTCCCCTATCAGCATCACATCAGCATTAGGGATG 120
 K  S  K  E  N  N  I  F  Y  S  P  I  S  I  T  S  A  L  G  M      40

GTCCTCTTAGGAGCCAAAGACAACACTGCACAACAGATTAAGAAGGTTCTTCACTTTGAT 180
 V  L  L  G  A  K  D  N  T  A  Q  Q  I  K  K  V  L  H  F  D      60

CAAGTCACAGAGAACACCACAGGAAAAGCTGCAACATATCATGTTGATAGGTCAGGAAAT 240
 Q  V  T  E  N  T  T  G  K  A  A  T  Y  H  V  D  R  S  G  N      80

GTTCATCACCAGTTTCAAAAGCTTCTGACTGAATTCAACAAATCCACTGATGCATATGAG 300
 V  H  H  Q  F  Q  K  L  L  T  E  F  N  K  S  T  D  A  Y  E     100

CTGAAGATCGCCAACAAGCTCTTCGGAGAAAAAACGTATCTATTTTTACAGGAATATTTA 360
 L  K  I  A  N  K  L  F  G  E  K  T  Y  L  F  L  Q  E  Y  L     120

GATGCCATCAAGAAATTTTACCAGACCAGTGTGGAATCTGTTGATTTTGCAAATGCTCCA 420
 D  A  I  K  K  F  Y  Q  T  S  V  E  S  V  D  F  A  N  A  P     140

GAAGAAAGTCGAAAGAAGATTAACTCCTGGGTGGAAAGTCAAACGAATGAAAAAATTAAA 480
 E  E  S  R  K  K  I  N  S  W  V  E  S  Q  T  N  E  K  I  K     160

AACCTAATTCCTGAAGGTAATATTGGCAGCAATACCACATTGGTTCTTGTGAACGCAATC 540
 N  L  I  P  E  G  N  I  G  S  N  T  T  L  V  L  V  N  A  I     180

TATTTCAAAGGGCAGTGGGAGAAGAAATTTAATAAAGAAGATACTAAAGAGGAAAAATTT 600
 Y  F  K  G  Q  W  E  K  K  F  N  K  E  D  T  K  E  E  K  F     200

TGGCCAAACAAGAATACATACAAGTCCATACAGATGATGAGGCAATACACATCTTTTCAT 660
 W  P  N  K  N  T  Y  K  S  I  Q  M  M  R  Q  Y  T  S  F  H     220

TTTGCCTCGCTGGAGGATGTACAGGCCAAGGTCCTGGAAATACCATACAAAGGCAAAGAT 720
 F  A  S  L  E  D  V  Q  A  K  V  L  E  I  P  Y  K  G  K  D     240

CTAAGCATGATTGTGTTGCTGCCAAATGAAATCGATGGTCTCCAGAAGCTTGAAGAGAAA 780
 L  S  M  I  V  L  L  P  N  E  I  D  G  L  Q  K  L  E  E  K     260

CTCACTGCTGAGAAATTGATGGAATGGACAAGTTTGCAGAATATGAGAGAGACACGTGTC 840
 L  T  A  E  K  L  M  E  W  T  S  L  Q  N  M  R  E  T  R  V     280

GATTTACACTTACCTCGGTTCAAAGTGGAAGAGAGCTATGACCTCAAGGACACGCTGAGA 900
 D  L  H  L  P  R  F  K  V  E  E  S  Y  D  L  K  D  T  L  R     300

ACCATGGGAATGGTGGATATCTTCAATGGGGATGCAGACCTCTCAGGCATGACCGGGAGC 960
 T  M  G  M  V  D  I  F  N  G  D  A  D  L  S  G  M  T  G  S     320

CGCGGTCTCGTGCTATCTGGAGTCCTACACAAGGCCTTTGTGGAGGTTACAGAGGAGGGA 1020
 R  G  L  V  L  S  G  V  L  H  K  A  F  V  E  V  T  E  E  G     340

GCAGAAGCTGCAGCTGCCACCGCTGTAGTAGCATTCGGATCATCACCTACTTCAACTAAT 1080
 A  E  A  A  A  A  T  A  V  V  A  F  G  S  S  P  T  S  T  N     360

GAAGAGTTCCATTGTAATCACCCTTTCCTATTCTTCATAAGGCAAAATAAGACCAACAGC 1140
 E  E  F  H  C  N  H  P  F  L  F  F  I  R  Q  N  K  T  N  S     380

ATCCTCTTCTATGGCAGATTCTCACCCCCGTAGATGCAATTAGTCTGTCACTCCATTTGG 1200
 I  L  F  Y  G  R  F  S  P  P                                    390

AAAATGTTCACCTGGAGATGTTCTGGTAAACTGATTGC 1238
```

FIG. 2 (SEQ ID NOS: 2 and 4)

USE OF A RECOMBINANT PROTEIN AS RECEPTOR OF A HEPATITIS VIRUS

CROSS REFERENCE TO RELATED APPLICATIONS

This application is based on application No. MI98A 000498 filed on Mar. 12, 1998 in Italy and U.S. Provisional Application No. 60/110,014 filed on Nov. 25, 1998, the content of which is incorporated hereinto by reference.

BACKGROUND OF THE INVENTION

This invention relates to the use of a recombinant protein as receptor for a hepatitis virus, a nucleic acid coding for it, a vector comprising said nucleic acid, a host cell transformed or transfected with said nucleic acid, a new recombinant protein possessing the biological property to act as receptor for a hepatitis virus, and a transgenic animal expressing said recombinant protein.

In particular, the present invention relates to the use of a recombinant protein as receptor for a hepatitis B virus, a nucleic acid coding for it, a vector comprising said nucleic acid, an host cell transformed or transfected with said nucleic acid, a new recombinant protein possessing the biological property to act as receptor for a hepatitis B virus, and a transgenic animal expressing said recombinant protein.

It is known that the hepatitis B disease is caused by the HBV virus (Hepatitis B Virus), belonging to the family named hepadnaviruses, that are viruses possessing a DNA molecule as genome capable to infect differentiated hepatocytes. Such viruses is able to infect humans only and higher primates in the evolutive scale (Ganem D. et al., "Ann. Rev. Biochem.", 56, 651–693, 1987).

The mechanism by which this non-cytolytic virus infects cells and induces liver damage, has not been completely understood up to now.

It is also known that the HBV has a genome endowed with unusual features of a small DNA molecule that is only partly double-strand and shows a single-strand region. The nucleocapsid, that encompasses the DNA, is essentially constituted by the core protein, also named HBcAg, which is able to interact with the viral DNA, and by a protein kinase able to phosphorylate the HBcAg protein. The virus has an envelope outside the core essentially composed of lipids and of three proteins, named Small (S), Medium (M) and Large (L), that constitute the surface antigen (HBsAg) of said virus (Tiollais P. et al., "Nature", 317, 489–495, 1985).

The viral envelope plays an essential role in the interaction process of the virus with the receptor protein occurring on the hepatocyte plasma membranes, since the virus/receptor interaction represents the first step of infectious process. In particular, it has been shown that the N terminal region, also named preS1, of the L viral protein is responsible for the virus/receptor interaction and indispensable for the entry of said virus into the hepatocyte (Neurath A. R. et al., "Cell", 46, 429–436, 1986).

At least 350 million persons are chronic carriers of hepatitis B. The chronic disease occurs, in part, in patients with acute hepatitis B infections and, almost always, in cases of asymptomatic infection. This latter situation occurs in particular in the children infected from the mothers at the birth, where the disease symptoms became evident only when the chronic state is already reached. In about 25–35% of chronic carriers, the disease develops irreversible hepatic complications, due to chronic active hepatitis, cirrhosis or primary hepatocarcinoma, that lead to the death of more than 1 million persons per year.

Up to now, a specific pharmacological therapy to treat hepatitis B patients did not exist (Gitlin N, "Clin. Chem.", 43, 1500–1506, 1997).

In the case of chronic carriers, for which it is important to intervene to avoid permanent hepatic damage, the only treatment, used up to now, is the administration of α-interferon. α-interferon shows a wide range of properties such as antiviral, antiproliferative, immunomodulatory, cytostatic and/or cytotoxic.

However, α-interferon therapy gives appreciable results only in the 30–40% of treated patients with chronic hepatitis. Furthermore, it is not possible to administer said molecule to all chronic carriers such as, for example, to patients showing high hepatic decompensation or portal hypertension or who are affected by autoimmune diseases.

The high species-specificity of HBV has not allowed developing an experimental model to study the infective process. In fact, the experimental system more utilized to study the HBV/hepatocyte interaction is represented by the use of human hepatocarcinoma cell line and named HepG2 (Knowles B. B. et al., "Nature", 209, 497–499, 1980).

Cells of HepG2 line have the advantage of not displaying the genome of integrated HBV, the ability to bind an HBV virus and to allow the entry of viral DNA into cytoplasm, thus showing the presence, on the plasmatic membrane, of a receptor molecule able to bind and internalize said virus. (Neurath A. R. et al., "Cell", 46, 429–436, 1986; Dash S. et al., "J. Med. Virol.", 37, 116–121, 1992).

However, the use of this cell line as the experimental model has the disadvantage that the virus is not able to replicate itself and thus generate new viral particles.

Given the high need to have a molecule with the biological properties to act as receptor for a hepatitis B virus, up to now, different molecules able to interact with the outer envelope of HVB have been tested, such as, for example, the 6-Interleukin (Neurath A. R. et al, "J. Exp. Med." 172, 461–469, 1992), the ASGPR receptor (Asialoglycoprotein) (Trechel U. et al., "J. Gen. Virol.", 75, 3021–3029, 1994), the receptor for the IgA (FcαR) (Pontisso P. et al.,"J. Gen. Virol." 73, 2041–2045, 1992), the GAPD (Glyceraldehyde-3-P-Dehydrogenase) (Petit M. A. et al., "Virology", 187, 211–222, 1992), the pHSA (polymerized Human Sera Albumin) (Pontisso P. et al., "J. Virol.", 63, 1981–1988, 1989), the HSSP (Human Soluble Serum Protein) (Bubkowska A. et al., "J. Virol.", 67, 4316–4322, 1993), the endonexin II (Hertogos K. et al., "Virology", 197, 549–557, 1993), the ApoH (Apolipoprotein H) (Mehdi H. et al., "J. Virol.", 68, 2415–2424, 1994).

However none of the above mentioned proteins has shown definitive and specific receptorial activity for the viral particles. Indeed a biological assay able to evidence the receptorial function of a protein is not available. Such biological assay should comprise the transfection of a cDNA coding for a protein, in a suitable cell line, and the subsequent verification of the susceptibility to the infection for cells expressing the recombinant receptor (Mendelsohn L. C. et al., "Cell", 56, 855–865, 1989; Bergelson J. M. et al., "Science", 275, 1320–1323, 1997).

Now, it has been unexpectably found that the human protein SCCA1 (Squamous Cell Carcinoma Antigen) of FIG. 1 (SEQ ID NOS: 1 and 3) has the ability to act as HBV receptor.

In addition, the inventors have also found an new allelic variant of SCCA1 (FIG. 2; SEQ ID NOS: 2 and 4).

SUMMARY OF THE INVENTION

Therefore, it is a first object of this invention to provide the use of a recombinant protein having, fully or in part, a primary structure as shown in FIG. 1 (SEQ ID NOS: 1 and 3) or 2 (SEQ ID NOS: 2 and 4), or of any allelic variant thereof, as a receptor for a hepatitis virus.

Preferably, said virus is a hepatitis B virus.

Recently, the methodologies of molecular screening based on combinatorial library have been used to identify new molecules with different biological activity, as new drugs. Typical example of such methodology is reported in Kenan D. L. et al ("Tibs", 2, 57–64, 1994). For the system HBV virus/receptor, such methodologies allow to the person skilled in the field to select, from a very high number of molecules, those able to neutralize the virus/receptor interaction and to evaluate subsequently their applicability in the pharmacological field.

It is therefore another object of the present invention to provide the use of a recombinant protein having, fully or in part, a primary structure as shown in FIG. 1 (SEQ ID NOS: 1 and 3) or 2 (SEQ ID NOS: 2 and 4), or of any allelic variant thereof, or of any its derivative having the biological property to act as a receptor for a hepatitis virus, in molecular screening assays.

The inventors' identification of a HBV receptor opens, the way to develop molecules with pharmacological activity able to neutralize the virus/receptor interaction occurring on the plasma membranes of hepatocytes and thus to inhibit the disease progression. This is obtained with methodologies known to the person skilled in the field. These are, for example, the use of the protein receptor as drug or as reagent for antibody production (monoclonal or polyclonal).

It is therefore a further object of present invention to provide the use of a recombinant protein having, fully or in part, a primary structure as shown in FIG. 1 (SEQ ID NOS: 1 and 3) or 2 (SEQ ID NOS: 2 and 4), or of any allelic variant thereof, or of any its derivative having the biological property to act as receptor for a hepatitis virus, as a drug.

Preferably, said drug is useful in the treatment of hepatitis B.

For monoclonal antibody production, for example, the procedure of Harlow and Lane may be ussed ["Antibodies", "A Laboratory Manual", Cold Spring Harbor Laboratory, Cold Spring Harbor, N.Y., (1988)] and the different monoclonal antibodies may be tested in clinical trials to evaluate their activity in different pathologies such as, for example, cancer (Bodey B. et al., "Anticancer Res.", 16, 661–674, 1996,), autoimmune diseases (Burmester G. R., "Baillieres Clin. Rheumatol.", 6, 415–434, 1992), and viral diseases (Co M. S. et al, "Proc. Natl. Acad. Sci.", 88, 2869–2873, 1991).

It is, therefore, another object of the present invention to provide the use of a recombinant protein having, fully or in part, a primary structure as shown in FIG. 1 (SEQ ID NOS: 1 and 3) or 2 (SEQ ID NOS: 2 and 4), or of any allelic variant thereof, or of any its derivative having the biological property to act as receptor for a hepatitis virus, in the production of monoclonal antibodies.

It is also an other object of the present invention to provide the use of a recombinant protein having, fully or in part, a primary structure as shown in FIG. 1 (SEQ ID NOS: 1 and 3) or 2 (SEQ ID NOS: 2 and 4), or of any allelic variant thereof, or of any its derivative having the biological property to act as receptor for a hepatitis virus, in the production of polyclonal antibodies.

In addition, the complete sequence of a nucleic acid (FIG. 2; SEQ ID NO: 2) able to code for a protein having the biological property to act as receptor for a hepatitis B virus has been synthesized starting from the nucleic acid sequence of the SCCA1.

It is, therefore, an other object of the present invention to provide an isolated nucleic acid that comprises a nucleic acid coding for a protein having, fully or in part, a primary structure showed in FIG. 1 (SEQ ID NOS: 1 and 3) or 2 (SEQ ID NOS: 2 and 4), or of any allelic variant thereof, provided, however, that said nucleic acid is not the nucleic acid showed in FIG. 1 (SEQ ID NO: 1).

Preferably, said nucleic acid codes for a protein having the biological property to act as receptor for a hepatitis B virus.

For the production of a recombinant protein having the biological property to act as receptor for a hepatitis B virus, expression systems both in prokaryotic and eukaryotic hosts may be used.

For the expression in prokaryotes, the nucleic acid coding for the recombinant protein is cloned in a suitable expression vector, such as for example pET21, and then introduced in a suitable bacterium, such as, for example *E. Coli*.

For the expression in eukaryotes, the nucleic acid coding for the recombinant protein, cloned in a suitable expression vector that allows stable or transient high expression levels, such as for example pcDNA3, is introduced in one of the large number of suitable mammalian cells.

It is therefore a further object of the present invention to provide a vector that comprises a nucleic acid coding for a protein having, fully or in part, a primary structure as shown in FIG. 1 (SEQ ID NOS: 1 and 3) or 2 (SEQ ID NOS: 2 and 4), or of any allelic variant thereof, provided, however, that said nucleic acid is not the nucleic acid shown in FIG. 1 (SEQ ID NO: 1).

It is also an object of the present invention to provide a prokaryotic or eukaryotic host cell permanently transformed or transfected with the above mentioned vector.

It is then an object of the present invention to provide an eukaryotic host cell constituting of the HepG2 cell line permanently transfected or transformed with a nucleic acid coding for a protein having, fully or in part, a primary structure as shown in FIG. 1 (SEQ ID NOS: 1 and 3) or 2 (SEQ ID NOS: 2 and 4), or of any allelic variant thereof.

It is a further object of the present invention to provide a recombinant protein having, fully or in part, a primary structure showed in FIG. 1 (SEQ ID NOS: 1 and 3) or 2 (SEQ ID NOS: 2 and 4), or of any allelic variant thereof, as a receptor for a hepatitis virus, provided, however, that the primary structure of said protein is not the protein as shown in FIG. 1 (SEQ ID NOS: 1 and 3).

The person skilled in the field can easily and routinely use the nucleic acid coding for the receptor protein for the hepatitis virus to generate transgenic animals, such as for example mice, expressing the receptor protein on the hepatocytes surface and thus inducing, in the animal, the human hepatitis infection.

Such animal models assume a remarkable pharmacological interest since they offer the possibility of an in vivo evaluation of the effect of the novel compounds with antiviral activity. Typical example of a known methodology for the generation of transgenic animals is described in Hogan et al. ("Manipulating the mouse embryo", Cold Spring Harbor Laboratory, 1986).

It is therefore another object of the present invention to provide a transgenic animal that is not an human being, characterized in that it expresses a recombinant protein having, fully or in part, a primary structure showed in FIG. 1 (SEQ ID NOS: 1 and 3) or 2 (SEQ ID NOS: 2 and 4), or of any allelic variant thereof.

Preferably, the above mentioned recombinant protein has the biological property to act as receptor for a hepatitis virus, and more preferably said receptor is a receptor for a hepatitis B virus.

The following Figures and the following Examples and Assays are intended to illustrate the present invention without limiting it in any way.

BRIEF DESCRIPTION OF THE DRAWING

FIG. 1 shows the nucleic acid sequence (SEQ ID NO: 1) and the corresponding amino acid sequence (SEQ ID NO: 3) of the recombinant protein SCCA1.

FIG. 2 shows the nucleic acid sequence (SEQ ID NO: 2) and the corresponding amino acid sequence (SEQ ID NO: 4) of the allelic variant G351-A, A357-T, S389-P.

DETAILED DESCRIPTION OF THE INVENTION

EXAMPLE 1

Production of the Recombinant SCCA1 Protein (Squamous Cell Carcinoma Antigen)

1) Isolation of the cDNA Coding for the SCCA1.

The complete cDNA sequence coding for the SCCA1 was isolated by the PCR technique (polymerase chain reaction) starting from the polyA$^+$ RNA extracted from human HepG2 cell line (Hepatocarcinoma) and preparing, on the basis of the known nucleotide sequence of SCCA1 (Suminami et al., "Biochem. Biophys. Res. Commun.", 181, 51–59, 1991) the oligonucleotides:

primer-1(sense): 5'CACAGGAGTTCCAGATCACATC-GAG (SEQ ID NO: 5);
primer-2 (antisense): 5'CTGGAAGAAAAAGTACATTTATATGTGGGC (SEQ ID NO: 6) respectively complementary to the regions −31/−7 and +1355/+1384 of the SCCA1 mRNA, and
primer-3 (sense): 5'GTTCACCATGAATTCACTCAGT-GAAGCC (SEQ ID NO: 7);
primer-4 (antisense): 5'GCAATCAGTTTACCAGAA-CATCTGCAG (SEQ ID NO: 8)

respectively complementary to the regions −7/+21 and +1212/+1238 of the SCCA1 mRNA that were used in the reaction of chain amplification.

For the production of the recombinant protein having the biological property to act as receptor for a hepatitis B virus, two different expression systems both in prokaryotic and eukaryotic hosts were used.

2) Production of the SCCA1 Recombinant Protein in a Prokaryotic Host (*E. Coli*).

The cDNA coding for the SCCA1 was cloned in the pET21a expression vector (NOVAGEN, Maidson, Wis., U.S.A. Cat. No. 69740-1). In this vector, the expression of cloned cDNA was monitored by the promoter recognized by the RNA polymerase of T7 bacteriophage, and the host *E.Coli* strain used was the BL21 (DE3)[F$^-$ ompT hsdS$_B$ (r$_B^-$m$_B^-$) gal dcm (DE3)] (NOVAGEN, Maidson, Wis., U.S.A. cat. n. 69387-1) engineered so that it contains in its genome a copy of the gene coding RNA polymerase of T7 bacteriophage.

Since the expression of the RNA polymerase of the T7 bacteriophage in BL21 (DE3) strain was controlled by the lacUV5 promoter, and the expression of the cDNA of interest, was negatively controlled by the lac operator sequence recognized by the laI repressor, it was possible to induce the expression of cDNA of interest by only adding IPTG (Isopropyl-β-D-Thiogalattopyranoside) in the culture medium. This double mechanism of control abolished the hazard of an eventual toxicity of the recombinant protein by the bacterial host. Further, in the first step of cloning, any possibility of expression of the cloned gene, by using a strain that does not express T7 RNA polymerase, was eliminated.

The pET21a vector allows the expression of fusion proteins showing, at the upstream and downstream position of the polylinker for the coding, sequences coding for two short fusion peptides of 11 and 6 amino acids respectively. Choosing in an appropriate manner the sites for the restriction enzymes to be used in the cloning procedure, it is possible to express also non fusion proteins and this possibility was used for the expression of SCCA1.

The pET21a vector was then digested with the restriction enzymes NdeI and BamHI (BOEHRINGER MANNHEIM, Mannhiem, Germany, Cat.No. 1-040-227 e Cat.No. 656-275) to eliminate the coding sequence for the 11 amino acids peptide located at the upstream position of the polylinker.

The cDNA sequence coding for the cloned SCCA1 was the one shown in FIG. 1 (SEQ ID NOS: 1 and 3), between the positions −1/+1238; it shows the stop sequence of the translation in position +1171/+1173. In such a manner, it was eliminated the possibility to translate into protein the short 6 amino acids peptide located at the downstrem position of the polylinker.

The fragment coding the receptor was prepared so as to show in 5' position an aligned extremity, while at the 3' extremity it was digested by the BamHI enzyme. In this way, the insert showed compatible extremities for the cloning in pET21a.

The reaction of ligation between the pET21a vector and the cDNA fragment coding for the receptor protein was prepared. The reaction mixture was put, by the transformation technique, into the XL1-blue-MRF' bacterial strain {Δ(mcrA) 183 Δ(mcrCB-hsdSMR-mrr) 173 endA1 supE44 thi-1 recA1 gyrA96 relA1 lac [F'proAB lacI$^q$ZΔM15 Tn10 (tet$^r$)]} (STRATAGENE, La Jolla, Calif., U.S.A., Cat. No. 200301), competent for the transformation by treatment with calcium chloride.

The transformed bacteria were selected by the resistance to the antibiotic ampicillin (BOEHRINGER MANNHEIM, Mannhiem, Germany, and Cat.No. 835-269), against which the pET21a vector confers resistance.

The confirmation of the cDNA cloning, expressing the HBV receptor, was obtained by sequencing with the Sanger dideoxynucleotides method, using the sequenase kit (AMHERSHAM, Little Chalfont, Buckinghamshire, UK, Cat. No. US 70770).

The recombinant plasmid was put, by the transformation technique, into the BL21 (DE3) expression strain, competent for the transformation by treatment with calcium chloride. A single bacterial colony of BL21(DE3) strain, containing the recombinant plasmid, was inoculated in 10 ml of LB (Lauria-Bertani Medium) culture medium [10 g/liter tryptone (OXOID, Basingstoke, U.K, Cat. No. L42), 5 g/liter yeast extract (ICN, Aurora, Ohio, U.S.A. Cat. No. 103303), 10 g/liter sodium chloride (SIGMA CHEMICAL COMPANY, Saint Louis, Mo., U.S.A., Cat. No. S7653) pH 7.2] containing ampicillin (100 μg/ml) at 37° C. for 16 hours under stirring to obtain a saturated culture. Then, the whole culture was added up to saturation, to 500 ml of LB containing ampicillin. The bacterial growth, performed at 37° C. under stirring, was monitored by a optical density spectrophometer at a wavelength of 600 nm. When the assorbance has reached a value of 0.6 units, the expression was induced by adding IPTG (SIGMA CHEMICAL COMPANY, Saint Louis, Mo., U.S.A., Cat. No. I5502) up to a concentration of 1 mM. The maximal expression of the recombinant protein SCCA1 was obtained after 4 hours from the induction, as verified by SDS-PAGE (Sodium Dodecyl Sulphate—Polyacrylamide Gel Electrophoresis) analysis.

A check, at the optical microscope, of the bacteria expressing the above mentioned protein allowed to show the formation of inclusion bodies, which is due both to the structural characteristic and to the high levels of recombinant protein expressed (about 300 mg of protein/liter of bacterial culture).

3) Production of Recombinant SCCA1 Protein in Eukaryotic Host.

To express the SCCA1 recombinant protein in eukaryotic hosts, the relative cDNA was cloned in the expression vector pcDNA3 (INVITROGEN BV, Leek, The Netherlands, Cat. No. V790-20) that allows high levels of stable or transient expression in many mammalian cells.

The cDNA of interest was cloned downstream to the strong human CMV (Cytomegalovirus) promoter and upstream to the BGH (Bovine Growth Hormone) poly-adenylation signal, that confer, respectively, high levels of expression and stability of the mRNA coding for the protein of interest. The possibility to obtain a stable expression was ensured by the presence, in the plasmid, of the neomycine resistance marker, which expression was under the control of the early promoter and of the SV40 poly-adenylation signal which makes the cells resistant against G418 antibiotic.

The cloning of cDNA was performed using two unique sites of endonuclease restriction occurring in the polylinker of pCDNA3 vector, and precisely the KpnI (BOEHRINGER MANNHEIM, Mannhiem, Germany, Cat.No. 742-953) as 5' site and the XbaI (BOEHRINGER MANNHEIM, Mannhiem, Germany, Cat.No. 674-265) as 3' site. These sites were chosen because they do not occur in the sequence coding for the desired protein and also because the cDNA sequence between the position −7/+1238 of FIG. 1 (SEQ ID NOS: 1 and 3) was previously cloned in the SmaI site of pUC18 vector (BOEHRINGER MANNHEIM, Mannhiem, Germany, Cat.No. 885-797) that shows, in its own polylinker, unique sites for KpnI and XbaI restriction enzymes at 5' and 3' of the cloning site of cDNA receptor, respectively. Thus, the pcDNA3 vector, digested with KpnI and XbaI, and the cDNA fragment for the HBV receptor, cloned in pUC18 and obtained by digestion with the same enzymes, were reacted in a ligation reaction.

By the ligation reaction, the transformed bacteria of XL1-blue-MRF' strain competent for the transformation by treatment with calcium chloride, were transformed. The transformed bacteria were selected by ampicillin antibody resistance against which the pcDNA3 vector confered resistance.

The happened cloning was verified by DNA preparation, enzymatic digestion to confirm the presence of the insert, and nucleotidic sequence with Sanger dideoxynucleotides method, the recombinant plasmid was transfected, by the calcium phosphate technique, in human HepG2 cell line and in CHO (Chinese Hamster Ovary) cell line, which were cultured by the following culture medium.

For the HepG2 cell line, the culture medium was EMEM (Eagle Minimum Essential Medium) (Cat. No. M2279), containing 10% FBS (Fetal Bovine Serum) (Cat. No. F7524), 1% NEAA (Non Essential Amino Acids) (Cat. No. M7245), glutamine 2 mM (Cat. No. G7513) and the mixture of penicillin/streptomycin (Cat.No. P0871) diluted 1:100. For the CHO cell line, the culture medium was DMEM (Dulbecco's Modified Eagle Medium) (Cat. No. D5671) containing 10% FBS (Fetal Bovine Serum) (Cat. No. F7524), 1% NEAA (Non Essential Amino Acids) (Cat. No. M7245), glutamine 2 mM (Cat. No. G7513), piruvate 1 mM (Cat.No S8636) and the mixture of penicillin/streptomycin (Cat.No. P0871) diluted 1:100. (All the reagents of the above mentioned culture medium were supplied by SIGMA CHEMICAL COMPANY, Saint Louis, Mo., U.S.A.).

24 hours before the transfection, HepG2 cells with a density of 50.000/cm$^2$ and CHO cells with a density of 10.000/cm$^2$ were plated.

4 hours before the transfection, the cells were washed with D-PBS (Dulbecco's Phosphate Buffered Saline) (SIGMA CHEMICAL COMPANY, Saint Louis, Mo., U.S.A., cat. n. D5527) and fresh medium was added. The transfection was performed with 20 μg of plasmid DNA for each petri dish having 10 cm of diameter in 1 ml of calcium phosphate solution. The DNA /calcium phosphate complex was allowed to contact the cells for 16 hours. The precipitate was removed, the cells were washed 3 times with D-PBS and fresh medium was added. After 72 hours of incubation, the screening of cells expressing the receptor was begun by adding the fresh medium added with G418 antibiotic (SIGMA CHEMICAL COMPANY, Saint Louis, Mo., U.S.A., Cat. No. G7034) at 0.6 mg/ml concentration for the HepG2 cell line and at a concentration of 0.75 mg/ml for CHO cell line and the selecting medium was replaced every 3 days.

For the HepG2 cell line, many single clones were detected 24 days later. 24 clones were picked from the selection plate and individually amplified in the condition described above. 15 days later, the G418 concentration was brought to 0.3 mg/ml.

For the CHO cell line, single clones were observed 22 days after the selection. 24 clones were picked from the selection plate and individually amplified in the condition described above. 7 days later, the antibiotic concentration was brought to 0.6 mg/ml.

To verify the expression of recombinant protein in the two transfected cell lines, western blot analysis was performed utilizing the soluble fraction of proteinic extracts obtained by freezing and unfreezing of the transfected cells. The antibody used to detect the band of the recombinant protein, was a polyclonal antibody purified an affinity column, generated in a immunizated rabbit with the recombinant protein obtained in bacteria. In many individually amplified clones, the antibody identified, in respect to the same non transfected cells and with the same amount of protein extracts loaded on gel, an added protein band having the expected molecular weight. For clones expressing the highest levels of receptor, its localization on the plasma membrane was observed by indirect immunofluorescence.

A clone, obtained from transfected HepG2 and a clone, obtained from transfected CHO were chosen, and these were further amplified to obtain high quantity of the soluble fraction of proteins extract to be used for the purification of recombinant protein.

EXAMPLE 2

Production of the Allelic Variant of the SCCA1 Recombinant Protein

The production and the purification of the allelic variant were carried out in a similar manner as the previous Example 1 with similar production and purification yields.

On the cDNA nucleotide sequence, coding for the SCCA1 protein, some point mutations were effected using the QuiKChange Site-directed Mutagenesis Kit (STRATAGENE, La Jolla, Calif., U.S.A., Cat. No. 200518) to obtain proteins with mutations simultaneously in more than one position, in order to establish their receptorial activity against the HBV viral particles present in the serum of patients in an acute infection stage.

Mutation of the three amino acids glycine 351, alanine 357 and serine 389 of the SCCA1 sequence, respectively in alanine 351, threonine 357 and proline 389, has allowed to obtain G351-A, A357-T, S389-P of SCCA1 (FIG. 2; SEQ ID NOS: 2 and 4). The receptorial activity of the allelic variant G351-A, A357-T, S389-P for the HBV viral particle, was demonstrated by infection assays performed on the cell lines transfected with the cDNA coding the mutated form of SCCA1.

EXAMPLE 3

Purification of SCCA1 Recombinant Protein

To purify the SCCA1 recombinant protein chromatographic methodologies utilizing three different approaches where used:
a) affinity chromatography by derivatizing a known chromatographic resin such as, for example, sepharose with polyclonal or monoclonal antibodies generated against the soluble form of the receptor;
b) affinity chromatography by derivatizing suitable matrix with a tetrameric peptide molecule that bind the soluble recombinant protein SCCA1. The above mentioned tetrameric peptide is named 4HBV[21-47] and shows 4 times the sequence between the amino acid 21 and 47 of the preS1 domain of the Large protein of the outer HBV envelope. Such sequence is that previously identified as essential for the binding of the virus to the receptor presents on the plasma membranes of the hepatocytes (Neurath A. R. et al., "Cell", 46, 429–436, 1986). The ability of this peptide molecule to bind the soluble form of the receptor was demonstrated by RIA assays contacting the 4HBV[21-47] molecule, labeled with iodine 125, with the receptor protein immobilized on the solid phase and counting the radioactivity associated to the receptor protein after repeated washing made for remove the excess of labeled molecule; and
c) ionic exchange chromatography and subsequent gel filtration.

Crude proteinic extracts containing the recombinant protein in soluble form were prepared to perform purification assays by the different approaches.

Crude extract coming from stable clones of eukaryotic cells expressing the recombinant protein, were obtained by repeated and quick cycles of freeze and thawing of the cells, and separation of the soluble fraction from the insoluble one by centrifugation. Western blot analysis of said fractions indicated that the majority of the protein was in the soluble fraction. This fraction could be used directly as it is for affinity chromatography.

On the contrary, stable clones of prokaryotic cells (bacteria), expressed the recombinant protein both in form of inclusion bodies and, therefore, in form of insoluble aggregate of recombinant protein, and in soluble form in the cytoplasmic fraction. The purification procedure has required the following further steps of solubilization of the inclusion bodies, while the cytoplasmic fraction was directly used.

After 4 hours from the induction of IPTG, the bacteria were collected by centrifugation and the bacterial pellet was washed 3 times with the saline buffer PBS (Phosphate Buffered Saline). The bacterial pellet was resuspended in PBS (4 ml/300 mg of pellet) and the suspension was sonicated with the Ultrasonic W-380 apparatus (immersion probe microtip 419A, f 4,8 mm manufactured by HEAT SYSTEMS ULTRASONICS, Farmingdale, N.Y., U.S.A.), setting up the following boost parameters 1', duty cycle 40%, output power 4. The sonication was extended up to the monitoring with an optical microscope has shown lysis of the 95–98% of bacteria was obtained.

The crude bacterial lysed were centrifuged at 15,000×g, at 4° C., for 45 minutes, to separate the soluble fraction from the insoluble one containing the inclusion bodies and the cellular debris. The insoluble fraction was resuspended in the same PBS volume wherein the sonication was carried out.

The solubilization was carried out by washing the inclusion bodies, removing PBS by centrifugation at 4000 rpm for 10 minutes, at room temperature, and resuspending the pellet with the same volume of water. The washing solution was again centrifuged, the water removed and the pellet treated one more time with water.

The recombinant protein in the inclusion bodies was then denatured with 5 volumes of 8M urea for 30 minutes at room temperature. The mixture of denaturation was centrifuged at 14,000 rpm for 10 minutes, at room temperature. The supernatant was filtered on a filter having pores with 0.45 μm diameter, and it was dialyzed against 50 mM Tris-HCl, pH 8 at 4° C. to remove the denaturing agent.

The dialyzed solution was further filtered on a filter having pores with 0.22 μm diameter, and by SDS-PAGE analysis, it was possible to verify that such procedure gives a recombinant protein having the biological property to act as HBV receptor, in a soluble form and already having a good purity level (about 80–90%).

Both the above mentioned crude proteic extracts obtained from eukaryotic transfected cells, and the above mentioned extracts obtained from prokaryotic transformed cells, were loaded on the affinity column. The fraction of the recombinant protein retained or from antibodies or from the 4HBV [21-47] ligand, was recovered changing the ionic strength or the pH of the buffer utilized, thus obtaining the recombinant protein in a pure form.

The purification of the recombinant protein produced in *E. Coli* at 37° C. in the cytoplasmic fraction, obtained after the sonication and centrifugation processes described above, was performed by a first step on a ionic exchange column and then on a molecular exclusion column.

1 ml of the supernatant was diluted with 1 ml of 20 mM Tris, pH 8,0 (loading buffer A) and loaded on a 1 ml ionic exchange column Resource Q (PHARMACIA, Cat. No. 17-1177-01). After recovering the unretained material, a saline gradient from 0 to 1M of NaCl in the A buffer was applied to the column, in 10 minutes, to allow the elution of the material retained by the column.

SDS-PAGE analysis of the eluted fractions showed that the recombinant protein was eluted with a high degree of purity, in the fraction corresponding to the material unretained by the column.

The entire fraction containing the protein (5 ml) was concentrated to 1 ml by ultrafiltration on Centriprep 3 unit (AMICON, Cat. No. 4302), and analysed by filtration on gel column Biosil Sec-250 (BIO-RAD, Cat. No.1250062). To determine the purity, the peak, eluted at the time corresponding to the molecular weight of the protein of interest (45,000 Da) was characterized by SDS-PAGE, RP-HPLC. The above mentioned peak was characterized with the Bio-Rad Protein Assay Kit (BIO-RAD, Cat. No. 500-0006) to determine the proteinic concentration.

The obtained data show that the protein was recovered in an amount of 450 µg for 1 ml of initial supernatant, with a purity degree higher than 95%.

Same results were obtained purifying the allelic variant G351-A, A357-T, S389-P, recombinant protein of FIG. 2 (SEQ ID NOS: 2 and 4).

EXAMPLE 4

Production of a Monoclonal Antibody Against the Recombinant Protein SCCA1

Balb/c mice (HARLAN NOSSAN, Milano, Italia), 4 weeks old, were immunized with 50 µg of the recombinant protein SCCA1 in soluble form, produced in eukaryotic cells as described in the previous Example 1.4 boosters were performed with the same quantity of recombinant receptor SCCA1, at two weeks intervals. The production of anti-protein receptor antibody was titrated after each booster by ELISA assays (Enzyme Like lmmunoadsorbent Assay) on microplates coated with the recombinant protein SCCA1 in solid phase. On the basis of the immuno-reactivity response, one mouse was selected for the preparation of hybridoma.

The mouse myeloma cells used to obtain the hybridoma were the NSO grown in the following conditions: DMEM (Cat. No. D5671), 10% FBS (Cat. No. F7524), 1% NEAA (Cat. No. M7245), 2 mM glutamine (Cat. No. G7513), and the mixture of 100 U/ml penicillin/streptomycin antibiotics (Cat.No. P0871). (All the above mentioned reagents were purchased from SIGMA CHEMICAL COMPANY, Saint Louis, Mo., U.S.A.).

These cells do not secrete any kind of antibodies and are negatively selected in the presence of cultural medium HAT (Hypoxantine Aminopterine Thymine; SIGMA CHEMICAL COMPANY, Saint Louis, Mo., U.S.A.; Cat. No. H-0262).

The mouse selected for the best immuno reactivity was sacrificed in a $CO_2$ chamber and under sterile conditions. The spleen was then taken removing the adherent adipose tissue, and washed with 10 ml of DMEM-GM (DMEM (Cat. No. D5671), 1% NEAA (Cat. No. M7245) and 2 mM glutamine (Cat. No. G7513)], reagents purchased from SIGMA CHEMICAL COMPANY, Saint Louis, Mo., U.S.A.). Then, the spleen was mechanically crushed and the obtained suspension was placed in a petri dish filled with 5 ml of DMEM-GM, pre warmed at 37° C. The suspension was crushed with a 5 ml pipette, the cells were recovered by centrifugation, washed always with the same cultural medium and counted in a Burker chamber.

The NSO myeloma cells were counted, resuspended in DMEM-GM culture medium and collected with the splenocytes in a ratio 1:5. The cells mixture was recovered by centrifugation, washed again with DMEM-GM adding to the recovered pellet, in 1 second, 1 ml of DMEM-GM containing 44% PEG (SIGMA CHEMICAL COMPANY, Saint Louis, Mo., U.S.A., Cat. No. P7777) that promotes the cellular fusion. In the 3 seconds, 2 ml of DMEM-GM were added and, after the resuspension of the pellet, 7 ml of DMEM-GM and 10% FBS (Sigma Chemical Company, Saint Louis, Mo., U.S.A., Cat. No. F7524) were added, obtaining a good mixing. The cells, recovered by centrifugation, were slowly and gently resuspended in 10 ml of DMEM-HAT (DMEM-GM and 15% FCS, 2% HAT 50 x (SIGMA CHEMICAL COMPANY, Saint Louis, Mo., U.S.A., Cat. No. H0262), 10% ESG (Ewing sarcoma growth factor) (COSTAR BIOLOGICALS, Sloterweg, The Netherlands) and 100 U/ml of penicillin/streptomycin mixture (Cat. No. P0871). The cells mixture was further diluted and plated on 96-well plates at 200.000 cells/well concentration.

About 15 days later, the supernatants of the clones, grown in the single wells, were assayed in ELISA assays to estimate the presence of antibodies able to recognize the viral receptor (recombinant protein).

The positive clones were further amplified, and the antibodies produced have been characterized by the determination of the isotype. The antibodies able to neutralize the virus/receptor binding were selected by ELISA assays, wherein the antibodies were used to compete with the virus/recombinant receptor binding coated on to microplates.

Following the same procedure, a monoclonal antibody against the allelic variant G351-A, A357-T, S389-P was produced.

ASSAY 1

Activity of the SCCA1 Recombinant Protein

To verify if the protein SCCA1 of FIG. 1 (SEQ ID NOS: 1 and 3) was able to bind the HBV virus and allowing it the entry in to the cell, the single clones of HepG2 and CHO, obtained from the G418 selection and chosen for their capability to express high levels of the recombinant protein having the biological property to act as receptor for a hepatitis virus, were contacted with the serum of patients with acute hepatitis B.

$1 \times 10^6$ cells, coming from confluent culture, were resuspended in 1.8 ml of complete culture medium. To this latter, 200 µl of HBV-DNA positive serum, wherein the viral DNA concentration was 4194 pg/ml, were added and the incubation was performed for 20 minutes at 37° C.

To remove the viral particles that did not interact with the cells, the sample was centrifuged at 800 rpm, for 5 minutes at room temperature. The supernatant was removed and the cells pellet was washed 4 times with PBS at room temperature to remove the viral particles bound to the cells in an aspecific way.

DNA was extracted from cells contacted with HBV by lysis of the cell themselves, obtained resuspending the pellet in a saline solution containing 1 mg/ml of proteinase K, and 0.1% SDS (Sodium Dodecyl Sulphate) and incubating for 60 minute at 37° C. The lysed mixture was extracted with the same volume of phenol saturated with TE [Tris-HCl 10 mM pH 7,5, EDTA 1 mM pH 8] to remove the protein fraction. The aqueous phase, recovered by centrifugation for 10 minutes, 3000 rpm at room temperature, was extracted again with the same volume of chloroform and recovered by centrifugation.

The thus extracted DNA was recovered by precipitation adding to the aqueous phase 0.3M sodium acetate and 2.5 volumes of cold absolute ethanol, and leaving the precipitation mixture over night at −20° C. The DNA was then recovered by centrifugation at 14.000 rpm, for 30 minutes, washed with 70% ethanol, and resuspended in sterile water.

Then, the presence of HBV DNA in samples of DNA extracted from the cells incubated with the virus, in the washing solution performed after the cells incubation with the positive HBV serum, and in the positive HBV serum used, was verified. Such verification was carried out by the quantitative determination of HBV-DNA with the molecular hybridization technique performed with specific probes and chemiluminiscent detection using the "HBV-DNA Hybrid Capture Kit" (Murex).

The obtained data have shown that the cell lines transfected with the DNA of the SCCA1 protein have HBV-DNA values at least 8 times higher than the control cell lines, indicating that the over-expression of the SCCA1 receptor protein is accompanied by an increase of virus capability to infect cells.

To confirm that the increase of HBV-DNA, obtained in the transfected HepG2 cells in comparison with the normal HepG2, and that the presence of HBV-DNA in transfected CHO cells, were due to a specific interaction of viral particles with the recombinant protein having receptorial function, the binding assays of the virus to the cells were repeated in the presence of anti-receptor polyclonal antibodies obtained as described above. The only difference in comparison with the above mentioned procedure was the addition of anti-receptor polyclonal antibody, in different concentrations, immediately before the addition of positive HBV-DNA serum.

The obtained data confirmed the receptorial functionality of the SCCA1 protein. In fact, the anti-SCCA1 polyclonal antibody, at the concentration of 1.0 μg/ml, are able to completely neutralize the viral infection.

Following the same procedure it was verified that the receptorial activity of the allelic variant G351-A, A357-T, S389-P is similar to the recombinant protein SCCA1 one.

ASSAY 2

Screening of Combinatorial Library

The recombinant protein SCCA1 and its allelic variant G351-A, A357-T, S389-P, were used as reagents for the screening of combinatorial library of different nature.

All this libraries displayed the characteristic to be formed by an enormous numbers of different molecules and were constituted by organic molecules such as, for example, peptides, proteins, modified oligonucleotides and oligosaccharides (Kenan D. L. et al "Tibs", 2, 57–64, 1994; Clackson T., "Tibtech", 12, 173–184, 1994). Therefore, these libraries have represented a powerful method to select ligands for the receptor and, in particular, for ligands able to neutralize the virus/receptor interaction.

The possible libraries could be subdivided substantially in two different groups: synthetic libraries, formed by organic compounds such as, for example, peptides and oligosaccharides, and biological libraries where the nucleotidic sequences coding for peptides or small proteins synthesized in laboratory, are expressed in bacteriophages, bacteria or yeast so as to be present on the surface of these organisms. Another type of library in the middle way between the synthetic and biological library, was defined "selex" (Tuerk C. et al., "Science", 249, 505–510, 1990) composed of the oligonucleotide molecules that when selected, are amplified and identified by cloning in bacteriophages.

The methodologies and the source of the receptor for the HBV virus varied on the base of the type of library utilized. The soluble libraries were directly utilized for the selection of molecules neutralizing the interaction between the HBV virus and the recombinant receptor expressed in the eukaryotic cells of stable clones, obtained as described above. Instead, the other type of libraries were used for the selection of ligands with the receptor and in in vitro assays such as, for example, ELISA assay and the Bio-panning procedure.

What is claimed is:

1. An isolated protein comprising the amino acid sequence in SEQ ID NO:4.

2. The isolated protein of claim 1 which is a hepatitis B virus receptor.

3. A method of screening for a substance which inhibits the interaction of a hepatitis B virus and a hepatitis B virus receptor comprising:

incubating said substance with said hepatitis B virus and said hepatitis B virus receptor; and detecting the presence or absence of an interaction between said hepatitis B virus and said hepatitis B virus receptor, wherein said hepatitis B virus receptor is an isolated protein comprising the amino acid sequence in SEQ ID NO:3, wherein the absence of an interaction between said hepatitis B virus and said hepatitis B virus receptor indicates the substance inhibits the interaction.

4. The method of claim 3, wherein said hepatitis B virus receptor is on the plasma membrane of a hepatocyte.

5. The method of claim 3, wherein said substance is an antibody.

6. A method of screening for a substance which inhibits the interaction of a hepatitis B virus and a hepatitis B virus receptor comprising:

incubating said substance with said hepatitis B virus and said hepatitis B virus receptor; and detecting the presence or absence of an interaction between said hepatitis B virus and said hepatitis B virus receptor, wherein said hepatitis B virus receptor is an isolated protein comprising the amino acid sequence in SEQ ID NO:4, wherein the absence of an between said B virus and said hepatitis B virus receptor indicates the substance inhibits the interaction.

7. The method of claim 6, wherein said hepatitis B virus receptor is on the plasma membrane of a hepatocyte.

8. The method of claim 6, wherein said substance is an antibody.

9. A method of binding to a hepatitis B virus comprising contacting an isolated protein selected from the group consisting of SEQ ID NO:3, and SEQ ID NO:4 with the hepatitis B virus.

10. The method of claim 9, wherein said contacting inhibits the binding of the hepatitis B virus to cell having a hepatitis B virus receptor.

11. The method of claim 10, wherein said cell is in a patient infected with a hepatitis B virus.

12. A method of inhibiting the binding of hepatitis B virus to a hepatitis B virus receptor comprising, obtaining an antibody which binds to an isolated protein selected from the group consisting of SEQ ID NO:3, SEQ ID NO:4, an antigenic fragment of SEQ ID NO:3, and an antigenic fragment of SEQ ID NO:4; wherein said antibody further inhibits the binding of hepatitis B virus to the hepatitis B virus receptor; and contacting said antibody with said hepatitis B virus receptor; wherein said contacting inhibits the binding of said hepatitis B virus to said hepatitis B virus receptor.

13. The method of claim 12, wherein said hepatitis B virus receptor is SEQ ID NO:3 or SEQ ID NO:4.

14. The method of claim 12, wherein said hepatitis B virus receptor is on the plasma membrane of a cell.

15. The method of claim 14, wherein said cell is in a patient infected with a hepatitis B virus.

* * * * *

SEQUENCE LISTING (1) GENERAL INFORMATION:

(iii) NUMBER OF SEQUENCES: 8

(2) INFORMATION FOR SEQ ID NO: 1:

(i) SEQUENCE CHARACTERISTICS:
      (A) LENGTH: 1245 base pairs
      (B) TYPE: nucleic acid
      (C) STRANDEDNESS: double
      (D) TOPOLOGY: linear (ii) MOLECULE TYPE: cDNA (iii) HYPOTHETICAL: NO (iv) ANTI-SENSE: NO (vi) ORIGINAL SOURCE:
      (A) ORGANISM: Squamous Cell Carcinoma Antigen
      (F) TISSUE TYPE: Hepatoma
      (G) CELL TYPE: Hepatocyte
      (H) CELL LINE: HepG2

(xi) SEQUENCE DESCRIPTION: SEQ ID NO: 1:

```
GTTCACCATG AATTCACTCA GTGAAGCCAA CACCAAGTTC ATGTTCGACC TGTTCCAACA      60

GTTCAGAAAA TCAAAAGAGA ACAACATCTT CTATTCCCCT ATCAGCATCA CATCAGCATT     120

AGGGATGGTC CTCTTAGGAG CCAAAGACAA CACTGCACAA CAGATTAAGA AGGTTCTTCA     180

CTTTGATCAA GTCACAGAGA ACACCACAGG AAAAGCTGCA ACATATCATG TTGATAGGTC     240
```

| | |
|---|---|
| AGGAAATGTT CATCACCAGT TTCAAAAGCT TCTGACTGAA TTCAACAAAT CCACTGATGC | 300 |
| ATATGAGCTG AAGATCGCCA ACAAGCTCTT CGGAGAAAAA ACGTATCTAT TTTTACAGGA | 360 |
| ATATTTAGAT GCCATCAAGA AATTTTACCA GACCAGTGTG GAATCTGTTG ATTTTGCAAA | 420 |
| TGCTCCAGAA GAAAGTCGAA AGAAGATTAA CTCCTGGGTG GAAAGTCAAA CGAATGAAAA | 480 |
| AATTAAAAAC CTCCTTCCTG AAGGTAATAT TGGCAGCAAT ACCACATTGG TTCTTGTGAA | 540 |
| CGCAATCTAT TTCAAAGGGC AGTGGGAGAA GAAATTTAAT AAAGAAGATA CTAAAGAGGA | 600 |
| AAAATTTTGG CCAAACAAGA ATACATACAA GTCCATACAG ATGATGAGGC AATACACATC | 660 |
| TTTTCATTTT GCCTCGCTGG AGGATGTACA GGCCAAGGTC CTGGAAATAC CATACAAAGG | 720 |
| CAAAGATCTA AGCATGATTG TGTTGCTGCC AAATGAAATC GATGGTCTCC AGAAGCTTGA | 780 |
| AGAGAAACTC ACTGCTGAGA AATTGATGGA ATGGACAAGT TTGCAGAATA TGAGAGAGAC | 840 |
| ACGTGTCGAT TTACACTTAC CTCGGTTCAA AGTGGAAGAA AGCTATGACC TCAAGGACAC | 900 |
| GTTGAGAACC ATGGGAATGG TGGATATCTT CAATGGGGAT GCAGACCTCT CAGGCATGAC | 960 |
| CGGGAGCCGC GGTCTCGTGC TATCTGGAGT CCTACACAAG GCCTTTGTGG AGGTTACAGA | 1020 |
| GGAGGGAGCA GAAGCTGCAG CTGCCACCGC TGTAGTAGGA TTCGGATCAT CACCTGCTTC | 1080 |
| AACTAATGAA GAGTTCCATT GTAATCACCC TTTCCTATTC TTCATAAGGC AAAATAAGAC | 1140 |
| CAACAGCATC CTCTTCTATG GCAGATTCTC ATCCCCGTAG ATGCAATTAG TCTGTCACTC | 1200 |
| CATTTGGAAA ATGTTCACCT GCAGATGTTC TGGTAAACTG ATTGC | 1245 |

(2) INFORMATION FOR SEQ ID NO: 2:

(i) SEQUENCE CHARACTERISTICS:
  (A) LENGTH: 1245 base pairs
  (B) TYPE: nucleic acid
  (C) STRANDEDNESS: double
  (D) TOPOLOGY: linear (ii) MOLECULE TYPE: cDNA (iii) HYPOTHETICAL: NO (iv) ANTI-SENSE: NO (vi) ORIGINAL SOURCE:
  (F) TISSUE TYPE: Hepatoma
  (G) CELL TYPE: Hepatocyte
  (H) CELL LINE: HepG2

(xi) SEQUENCE DESCRIPTION: SEQ ID NO: 2:

| | |
|---|---|
| GTTCACCATG AATTCACTCA GTGAAGCCAA CACCAAGTTC ATGTTCGACC TGTTCCAACA | 60 |
| GTTCAGAAAA TCAAAAGAGA ACAACATCTT CTATTCCCCT ATCAGCATCA CATCAGCATT | 120 |
| AGGGATGGTC CTCTTAGGAG CCAAAGACAA CACTGCACAA CAGATTAAGA AGGTTCTTCA | 180 |
| CTTTGATCAA GTCACAGAGA ACACCACAGG AAAAGCTGCA ACATATCATG TTGATAGGTC | 240 |
| AGGAAATGTT CATCACCAGT TTCAAAAGCT TCTGACTGAA TTCAACAAAT CCACTGATGC | 300 |
| ATATGAGCTG AAGATCGCCA ACAAGCTCTT CGGAGAAAAA ACGTATCTAT TTTTACAGGA | 360 |
| ATATTTAGAT GCCATCAAGA AATTTTACCA GACCAGTGTG GAATCTGTTG ATTTTGCAAA | 420 |
| TGCTCCAGAA GAAAGTCGAA AGAAGATTAA CTCCTGGGTG GAAAGTCAAA CGAATGAAAA | 480 |
| AATTAAAAAC CTCCTTCCTG AAGGTAATAT TGGCAGCAAT ACCACATTGG TTCTTGTGAA | 540 |
| CGCAATCTAT TTCAAAGGGC AGTGGGAGAA GAAATTTAAT AAAGAAGATA CTAAAGAGGA | 600 |
| AAAATTTTGG CCAAACAAGA ATACATACAA GTCCATACAG ATGATGAGGC AATACACATC | 660 |

-continued

```
TTTTCATTTT GCCTCGCTGG AGGATGTACA GGCCAAGGTC CTGGAAATAC CATACAAAGG      720

CAAAGATCTA AGCATGATTG TGTTGCTGCC AAATGAAATC GATGGTCTCC AGAAGCTTGA      780

AGAGAAACTC ACTGCTGAGA AATTGATGGA ATGGACAAGT TTGCAGAATA TGAGAGAGAC      840

ACGTGTCGAT TTACACTTAC CTCGGTTCAA AGTGGAAGAG AGCTATGACC TCAAGGACAC      900

GTTGAGAACC ATGGGAATGG TGGATATCTT CAATGGGGAT GCAGACCTCT CAGGCATGAC      960

CGGGAGCCGC GGTCTCGTGC TATCTGGAGT CCTACACAAG GCCTTTGTGG AGGTTACAGA     1020

GGAGGGAGCA GAAGCTGCAG CTGCCACCGC TGTAGTAGCA TTCGGATCAT CACCTACTTC     1080

AACTAATGAA GAGTTCCATT GTAATCACCC TTTCCTATTC TTCATAAGGC AAAATAAGAC     1140

CAACAGCATC CTCTTCTATG GCAGATTCTC ACCCCCGTAG ATGCAATTAG TCTGTCACTC     1200

CATTTGGAAA ATGTTCACCT GCAGATGTTC TGGTAAACTG ATTGC                     1245
```

(2) INFORMATION FOR SEQ ID NO: 3:

(i) SEQUENCE CHARACTERISTICS:
        (A) LENGTH: 390 amino acids
        (B) TYPE: amino acid
        (C) STRANDEDNESS: single
        (D) TOPOLOGY: linear (ii) MOLECULE TYPE: protein (iii) HYPOTHETICAL: NO (iv) ANTI-SENSE: NO (xi) SEQUENCE DESCRIPTION: SEQ ID NO: 3:

```
Met Asn Ser Leu Ser Glu Ala Asn Thr Lys Phe Met Phe Asp Leu Phe
1               5                  10                  15

Gln Gln Phe Arg Lys Ser Lys Glu Asn Asn Ile Phe Tyr Ser Pro Ile
            20                  25                  30

Ser Ile Ile Ser Ala Leu Gly Met Val Leu Leu Gly Ala Lys Asp Asn
        35                  40                  45

Thr Ala Gln Gln Ile Lys Lys Val Leu His Phe Asp Gln Val Thr Glu
    50                  55                  60

Asn Thr Thr Gly Lys Ala Ala Thr Tyr His Val Asp Arg Ser Gly Asn
65                  70                  75                  80

Val His His Gln Phe Gln Lys Leu Leu Thr Glu Phe Asn Lys Ser Thr
                85                  90                  95

Asp Ala Tyr Glu Leu Lys Ile Ala Asn Lys Leu Phe Gly Glu Lys Thr
            100                 105                 110

Tyr Leu Phe Leu Gln Glu Tyr Leu Asp Ala Ile Lys Lys Phe Tyr Gln
        115                 120                 125

Thr Ser Val Glu Ser Val Asp Phe Ala Asn Ala Pro Glu Glu Ser Pro
    130                 135                 140

Lys Lys Ile Asn Ser Trp Val Glu Ser Gln Thr Asn Glu Lys Ile Lys
145                 150                 155                 160

Asn Leu Ile Pro Glu Gly Asn Ile Gly Ser Asn Thr Thr Leu Val Leu
                165                 170                 175

Val Asn Ala Ile Tyr Phe Lys Gly Gln Trp Glu Lys Lys Phe Asn Lys
            180                 185                 190

Glu Asp Thr Lys Glu Glu Lys Phe Trp Pro Asn Lys Asn Thr Tyr Lys
        195                 200                 205

Ser Ile Gln Met Met Arg Gln Tyr Thr Ser Phe His Phe Ala Ser Leu
    210                 215                 220
```

```
Glu Asp Val Gln Ala Lys Val Leu Glu Ile Pro Tyr Lys Gly Lys Asp
225                 230                 235                 240

Leu Ser Met Ile Val Leu Pro Asn Glu Ile Asp Gly Leu Gln Lys
            245                 250                 255

Leu Glu Glu Lys Leu Thr Ala Glu Lys Leu Met Glu Trp Thr Ser Leu
            260                 265                 270

Gln Asn Met Arg Glu Thr Arg Val Asp Leu His Leu Pro Arg Phe Lys
            275                 280                 285

Val Glu Glu Ser Tyr Asp Leu Lys Asp Thr Leu Arg Thr Met Gly Met
290                 295                 300

Val Asp Ile Phe Asn Gly Asp Ala Asp Leu Ser Gly Met Thr Gly Ser
305                 310                 315                 320

Arg Gly Leu Val Leu Ser Gly Val Leu His Lys Ala Phe Val Glu Val
            325                 330                 335

Thr Glu Glu Gly Ala Glu Ala Ala Ala Thr Ala Val Val Gly Phe
            340                 345                 350

Gly Ser Ser Pro Ala Ser Thr Asn Glu Glu Phe His Cys Asn His Pro
            355                 360                 365

Phe Leu Phe Phe Ile Arg Gln Asn Lys Thr Asn Ser Ile Leu Phe Tyr
370                 375                 380

Gly Arg Phe Ser Ser Pro
385                 390

(2) INFORMATION FOR SEQ ID NO: 4:

(i) SEQUENCE CHARACTERISTICS:
        (A) LENGTH: 390 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO: 4:

Met Asn Ser Leu Ser Glu Ala Asn Thr Lys Phe Met Phe Asp Leu Phe
1               5                   10                  15

Gln Gln Phe Arg Lys Ser Lys Glu Asn Asn Ile Phe Tyr Ser Pro Ile
            20                  25                  30

Ser Ile Ile Ser Ala Leu Gly Met Val Leu Leu Gly Ala Lys Asp Asn
            35                  40                  45

Thr Ala Gln Gln Ile Lys Lys Val Leu His Phe Asp Gln Val Thr Glu
50                  55                  60

Asn Thr Thr Gly Lys Ala Ala Thr Tyr His Val Asp Arg Ser Gly Asn
65                  70                  75                  80

Val His His Gln Phe Gln Lys Leu Leu Thr Glu Phe Asn Lys Ser Thr
                85                  90                  95

Asp Ala Tyr Glu Leu Lys Ile Ala Asn Lys Leu Phe Gly Glu Lys Thr
            100                 105                 110

Tyr Leu Phe Leu Gln Glu Tyr Leu Asp Ala Ile Lys Lys Phe Tyr Gln
            115                 120                 125

Thr Ser Val Glu Ser Val Asp Phe Ala Asn Ala Pro Glu Glu Ser Pro
            130                 135                 140

Lys Lys Ile Asn Ser Trp Val Glu Ser Gln Thr Asn Glu Lys Ile Lys
145                 150                 155                 160

Asn Leu Ile Pro Glu Gly Asn Ile Gly Ser Asn Thr Thr Leu Val Leu
```

```
                    165                 170                 175
Val Asn Ala Ile Tyr Phe Lys Gly Gln Trp Glu Lys Phe Asn Lys
                180                 185                 190

Glu Asp Thr Lys Glu Lys Phe Trp Pro Asn Lys Asn Thr Tyr Lys
                195                 200                 205

Ser Ile Gln Met Met Arg Gln Tyr Thr Ser Phe His Phe Ala Ser Leu
                210                 215                 220

Glu Asp Val Gln Ala Lys Val Leu Glu Ile Pro Tyr Lys Gly Lys Asp
225                 230                 235                 240

Leu Ser Met Ile Val Leu Leu Pro Asn Glu Ile Asp Gly Leu Gln Lys
                    245                 250                 255

Leu Glu Glu Lys Leu Thr Ala Glu Lys Leu Met Glu Trp Thr Ser Leu
                260                 265                 270

Gln Asn Met Arg Glu Thr Arg Val Asp Leu His Leu Pro Arg Phe Lys
                275                 280                 285

Val Glu Glu Ser Tyr Asp Leu Lys Asp Thr Leu Arg Thr Met Gly Met
                290                 295                 300

Val Asp Ile Phe Asn Gly Asp Ala Asp Leu Ser Gly Met Thr Gly Ser
305                 310                 315                 320

Arg Gly Leu Val Leu Ser Gly Val Leu His Lys Ala Phe Val Glu Val
                    325                 330                 335

Thr Glu Glu Gly Ala Glu Ala Ala Ala Thr Ala Val Val Ala Phe
                340                 345                 350

Gly Ser Ser Pro Thr Ser Thr Asn Glu Glu Phe His Cys Asn His Pro
                    355                 360                 365

Phe Leu Phe Phe Ile Arg Gln Asn Lys Thr Asn Ser Ile Leu Phe Tyr
                370                 375                 380

Gly Arg Phe Ser Pro Pro
385                 390
```

(2) INFORMATION FOR SEQ ID NO: 5:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 5:

CACAGGAGTT CCAGATCACA TCGAG                                    25

(2) INFORMATION FOR SEQ ID NO: 6:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: YES (xi) SEQUENCE DESCRIPTION: SEQ ID NO: 6:

-continued

```
CTGGAAGAAA AAGTACATTT ATATGTGGGC                    30
```

(2) INFORMATION FOR SEQ ID NO: 7:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 7:

```
GTTCACCATG AATTCACTCA GTGAAGCC                      28
```

(2) INFORMATION FOR SEQ ID NO: 8:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: YES (xi) SEQUENCE DESCRIPTION: SEQ ID NO: 8:

```
GCAATCAGTT TACCAGAACA TCTGCAG                       27
```